US011830185B2

(12) United States Patent
Aoyama

(10) Patent No.: US 11,830,185 B2
(45) Date of Patent: Nov. 28, 2023

(54) MEDICAL IMAGE PROCESSING SYSTEM AND LEARNING METHOD

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 483 days.

(21) Appl. No.: 17/225,872

(22) Filed: Apr. 8, 2021

(65) Prior Publication Data
US 2021/0224989 A1 Jul. 22, 2021

Related U.S. Application Data

(63) Continuation of application No. PCT/JP2019/040247, filed on Oct. 11, 2019.

(30) Foreign Application Priority Data

Oct. 16, 2018 (JP) .................................. 2018-195034

(51) Int. Cl.
G16H 50/20 (2018.01)
G06T 7/00 (2017.01)
G16H 30/40 (2018.01)

(52) U.S. Cl.
CPC ........... *G06T 7/0012* (2013.01); *G16H 30/40* (2018.01); *G16H 50/20* (2018.01); *G06T 2207/20081* (2013.01); *G06T 2207/30096* (2013.01)

(58) Field of Classification Search
CPC ......... G06T 7/0012; G06T 2207/20081; G06T 2207/30096; G06T 7/11; G06T 2207/10068; G06T 2207/20084; G06T 2207/30028; G16H 30/40; G16H 50/20; A61B 1/00; A61B 1/045
(Continued)

(56) References Cited

U.S. PATENT DOCUMENTS

2012/0177259 A1 7/2012 Hirota et al.
2013/0051680 A1 2/2013 Kono et al.
(Continued)

FOREIGN PATENT DOCUMENTS

| JP | 2012143340 A | 8/2012 |
|----|--------------|--------|
| WO | 2017002184 A1 | 1/2017 |
| WO | 2018008593 A1 | 1/2018 |

OTHER PUBLICATIONS

The extended European search report issued by the European Patent Office dated Nov. 5, 2021, which corresponds to European Patent Application No. 19873567.2-1126 and is related to U.S. Appl. No. 17/225,872.
(Continued)

Primary Examiner — Charlotte M Baker
(74) Attorney, Agent, or Firm — Studebaker & Brackett PC

(57) ABSTRACT

An effective diagnosis region detection unit uses an effective diagnosis region detection model and detects an effective diagnosis region in which a non-target region of interest other than a region of interest is removed from an observation target, from a first medical image. The effective diagnosis region detection model is obtained by learning using first learning data including the first medical image and effective diagnosis region information regarding the effective diagnosis region. The region-of-interest detection unit detects the region of interest from the effective diagnosis region.

9 Claims, 9 Drawing Sheets

(58) Field of Classification Search
USPC .......................................................... 382/128
See application file for complete search history.

(56) References Cited

U.S. PATENT DOCUMENTS

| | | |
|---|---|---|
| 2016/0007830 A1 | 1/2016 | Chun |
| 2018/0114319 A1 | 4/2018 | Kono et al. |
| 2019/0236497 A1* | 8/2019 | Santos .................... G06F 17/18 |

OTHER PUBLICATIONS

International Search Report issued in PCT/JP2019/040247; dated Dec. 10, 2019.
International Preliminary Report On Patentability and Written Opinion issued in PCT/JP2019/040247; dated Apr. 14, 2021.
Funke, Isabel et al., Generative adversarial networks for specular highlight removal in endoscopic images, Proceedings of SPIE, Mar. 12, 2018, vol. 10576, pp. 1-9, ISSN: 0277-786X, DOI: 10. 1117/12. 2293755.
Chen, Honghan et al., Automatic content understanding with cascaded spatial-temporal deep framework for capsule endoscopy videos, Neurocomputing, 2017, vol. 229, pp. 77-87, ISSN: 0925-2312, DOI: 10. 1016/j.eucom.2016.06.077.
Rodriguez-Sanchez, Antonio et al., A deep learning approach for detecting and correcting highlights in endoscopic images, 2017 Seventh International Conference on Image Processing Theory, Tools and Applications (IPTA), 2017, ISSN: 2154-512X, DOI: 10. 1109/IPTA. 2017.8310082.

\* cited by examiner

MEDICAL IMAGE PROCESSING SYSTEM AND LEARNING METHOD

CROSS-REFERENCE TO RELATED APPLICATIONS

This application is a Continuation of PCT International Application No. PCT/JP2019/040247 filed on 11 Oct. 2019, which claims priority under 35 U.S.C § 119(a) to Japanese Patent Application No. 2018-195034 filed on 16 Oct. 2018. The above application is hereby expressly incorporated by reference, in its entirety, into the present application.

BACKGROUND OF THE INVENTION

1. Field of the Invention

The present invention relates to a medical image processing system and a learning method that use analysis results of a medical image.

2. Description of the Related Art

In the current medical field, medical image processing systems that use medical images, such as an endoscope system comprising a light source device, an endoscope, and a processor device, are widespread. Further, in recent years, diagnostic information on a pathological condition has been acquired by extracting a region of interest that may be a lesion area from a medical image and performing image analysis on the extracted region of interest.

In a medical image used for detecting a region of interest, in addition to the region of interest such as a lesion, a non-target region of interest other than the region of interest such as a dark area, a blur, a residue, and a specular reflection may be reflected. The existence of such a non-target region of interest hinders the detection of the region of interest and is one of factors that reduce detection accuracy of the region of interest. On the other hand, in WO2017/002184A (corresponding to US2018/0114319A1), a region of interest is detected based on the color feature, contour, shape, texture, and the like after removing a non-target region of interest based on the color feature and frequency component. Further, in JP2012-143340A (corresponding to US2012/0177259A1), in a case where a region of interest is a mucosal region, either the mucosal region or a non-mucosal region such as a residue is discriminated by using a color and a feature amount of an edge. Further, in WO2018/008593A, after removing an inappropriate region such as shine from a medical image, an abnormal region in the image corresponding to a region of interest is detected. In WO2018/008593A, a region in which a pixel value exceeds a threshold value T is removed as an inappropriate region.

SUMMARY OF THE INVENTION

As described above, in removing a non-target region of interest from a medical image, in a case where a specific image feature amount such as a color feature amount and a pixel value is used as in WO2017/002184A, JP2012-143340A, and WO2018/008593A, it is necessary to individually deal with changes of the non-target region of interest due to observation conditions, illumination conditions, and the like, and it is difficult to reliably remove the non-target region of interest. Therefore, instead of specifying and using the image feature amount of the medical image as in WO2017/002184A, JP2012-143340A, and WO2018/008593A, it has been required to improve detection accuracy of a region of interest by specifying a non-target region of interest and detecting the region of interest from a region in which the non-target region of interest is removed.

An object of the present invention is to provide a medical image processing system and a learning method capable of specifying a non-target region of interest other than a region of interest without specifying an image feature amount of a medical image in detecting the region of interest from the medical image.

According to an aspect of the present invention, there is provided a medical image processing system comprising: a medical image acquisition unit that acquires a first medical image obtained by imaging an observation target; an effective diagnosis region detection unit that detects an effective diagnosis region in which a non-target region of interest other than a region of interest is removed from the observation target, from the first medical image; and a region-of-interest detection unit that detects the region of interest from the effective diagnosis region, in which the effective diagnosis region detection unit detects the effective diagnosis region from the first medical image, by using an effective diagnosis region detection model obtained by learning using first learning data including the first medical image and effective diagnosis region information regarding the effective diagnosis region.

It is preferable that the region-of-interest detection unit detects the region of interest from the effective diagnosis region, by using a region-of-interest detection model obtained by learning using second learning data including the effective diagnosis region and the region of interest. It is preferable that the first medical image is obtained by imaging an observation target illuminated with white light. It is preferable that the medical image acquisition unit acquires a second medical image different from the first medical image, and the region-of-interest detection unit detects the region of interest from the effective diagnosis region of the second medical image. It is preferable that the second medical image is obtained by imaging an observation target illuminated with blue narrow-band light. The non-target region of interest includes a puddle, a blood pool, a dark area, a specular reflection, distortion, image blur, a bubble, a cap, a residue, and a residual liquid.

According to another aspect of the present invention, there is provided a medical image processing system comprising: a registration unit that registers first learning data including a first medical image obtained by imaging an observation target and effective diagnosis region information regarding an effective diagnosis region in which a non-target region of interest other than a region of interest is removed from the observation target; and a learning unit that performs learning for generating an effective diagnosis region detection model that outputs the effective diagnosis region in response to an input of the first medical image, by using a plurality of pieces of the first learning data.

It is preferable that the registration unit registers second learning data including the effective diagnosis region and the region of interest, and the learning unit performs learning for generating a region-of-interest detection model that outputs the region of interest in response to an input of the effective diagnosis region, by using the second learning data.

According to another aspect of the present invention, there is provided a learning method comprising: a first learning step of performing, by a learning unit, learning for generating an effective diagnosis region detection model that outputs an effective diagnosis region in response to an input of a first medical image, by using a plurality of pieces of first learning data including the first medical image obtained by imaging an observation target and effective diagnosis region information regarding the effective diagnosis region in which a non-target region of interest other than a region of interest is removed from the observation target.

The learning method further comprises: a second learning step of performing, by the learning unit, learning for generating a region-of-interest detection model that outputs the region of interest in response to an input of the effective diagnosis region, by using a plurality of pieces of second learning data including the effective diagnosis region and the region of interest.

According to the aspects of the present invention, it is possible to specify a non-target region of interest other than a region of interest without specifying an image feature amount of a medical image in detecting the region of interest from the medical image.

BRIEF DESCRIPTION OF THE DRAWINGS

FIG. 1 is a block diagram showing an image processing system, an endoscope system, and the like.

DESCRIPTION OF THE PREFERRED EMBODIMENTS

Figure 1:
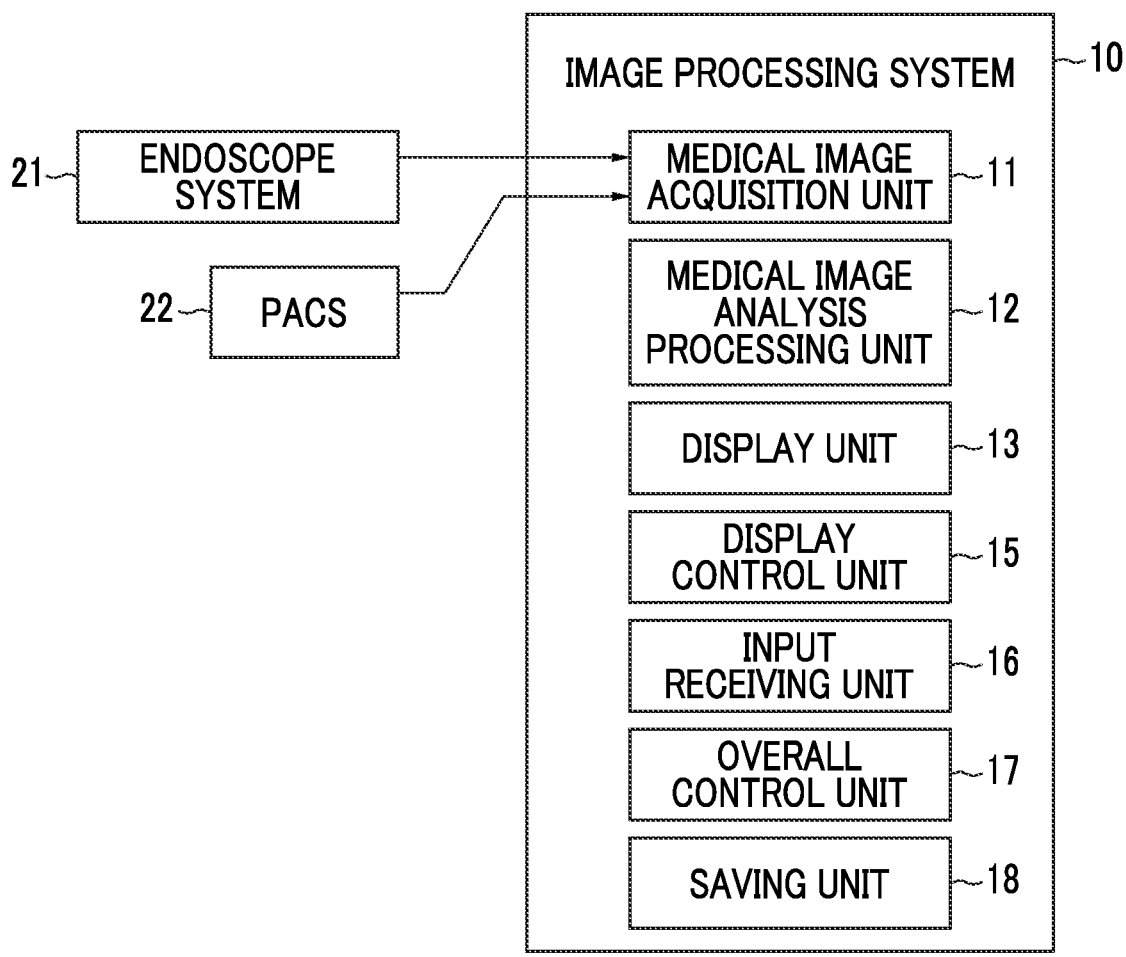

As shown in FIG. 1, an image processing system 10 comprises a medical image acquisition unit 11, a medical image analysis processing unit 12, a display unit 13, a display control unit 15, an input receiving unit 16, an overall control unit 17, and a saving unit 18.

The medical image acquisition unit 11 acquires a medical image including a subject image, directly from an endoscope system 21 or the like that is a medical apparatus, or through a management system such as a picture archiving and communication system (PACS) 22, or other information systems. The medical image is a still image or a motion picture (a so-called examination motion picture). In a case where the medical image is a motion picture, the medical image acquisition unit 11 can acquire a frame image forming a motion picture after examination as a still image. In addition, in a case where the medical image is a motion picture, display of the medical image includes not only displaying a still image of one representative frame forming the motion picture but also reproducing the motion picture once or multiple times. In addition, the medical image acquired by the medical image acquisition unit 11 includes an image automatically captured by a medical apparatus such as the endoscope system 21 regardless of a capturing instruction of a doctor, in addition to an image captured by the doctor using a medical apparatus such as the endoscope system 21. In the present embodiment, since both the image processing system 10 and the endoscope system 21 perform image processing using medical images, both the image processing system 10 and the endoscope system 21 correspond to a medical image processing system. The medical image processing system also includes an ultrasonic diagnostic apparatus that acquires and displays an image in real time.

In the case of being capable of acquiring a plurality of medical images, the medical image acquisition unit 11 can selectively acquire one or a plurality of medical images among these medical images. In addition, the medical image acquisition unit 11 can acquire a plurality of medical images acquired in a plurality of different examinations. For example, it is possible to acquire one or both of a medical image acquired in an examination performed in the past and a medical image acquired in the latest examination. That is, the medical image acquisition unit 11 can acquire a medical image optionally.

In the present embodiment, a plurality of medical images each including a subject image are acquired. More specifically, in a case where a medical image captured in one specific examination is acquired and there are a plurality of medical images captured in one specific examination, a plurality of medical images are acquired out of a series of medical images. In addition, in the present embodiment, the image processing system 10 is connected to the endoscope system 21 to acquire a medical image from the endoscope system 21. That is, in the present embodiment, the medical image is an endoscopic image.

The display unit 13 is a display for displaying the medical image acquired by the medical image acquisition unit 11 and an analysis result of the medical image analysis processing unit 12. A monitor or a display included in a device or the like to which the image processing system 10 is connected can be shared and used as the display unit 13 of the image processing system 10. The display control unit 15 controls a display form of the medical image and the analysis result on the display unit 13.

The input receiving unit 16 receives inputs from a mouse, a keyboard, and other operation devices connected to the image processing system 10. An operation of each unit of the image processing system 10 can be controlled using the operation devices.

The overall control unit 17 controls the overall operation of each unit of the image processing system 10. In a case where the input receiving unit 16 receives an operation input using an operation device, the overall control unit 17 controls each unit of the image processing system 10 according to the operation input.

The saving unit 18 saves a still image or the like of a medical image in a storage device (not shown) such as a memory included in the image processing system 10 or a storage device (not shown) included in a medical apparatus such as the endoscope system 21 or the PACS 22.

Figure 2:
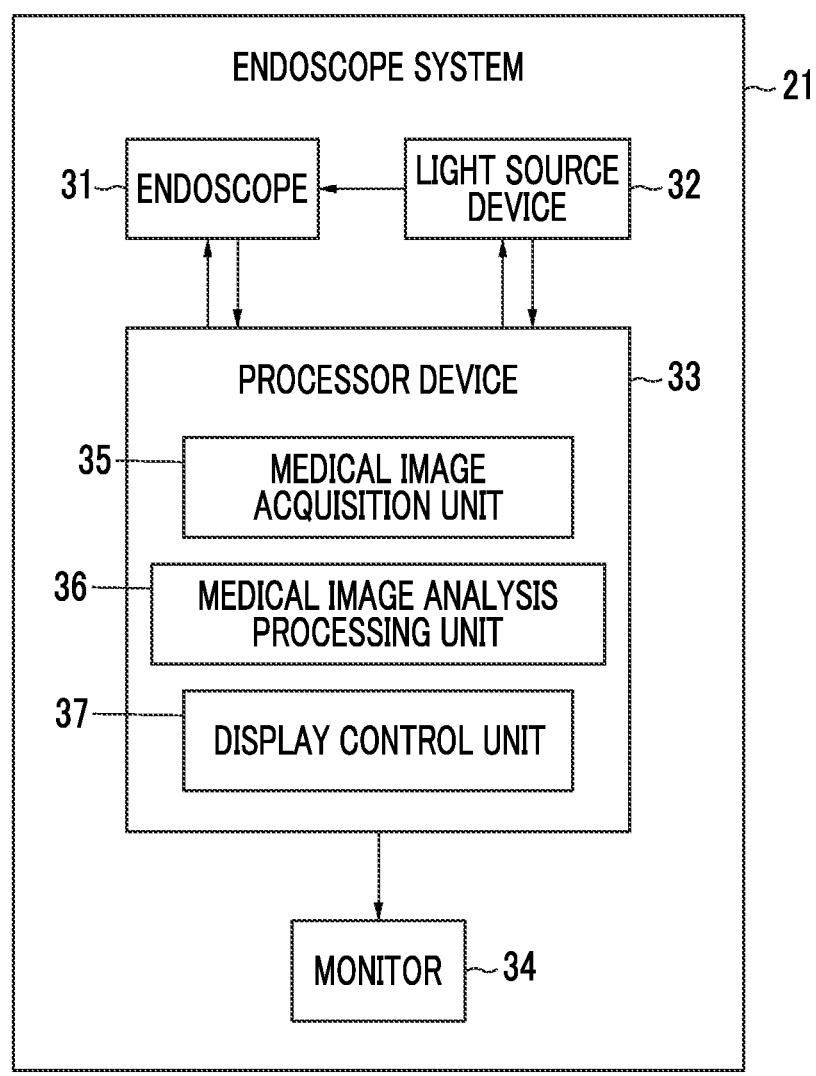
FIG. 2 is a block diagram showing the endoscope system.

As shown in FIG. 2, in the present embodiment, the endoscope system 21 to which the image processing system 10 is connected includes an endoscope 31 that acquires an image by emitting at least one of light in a white wavelength band or light in a specific wavelength band to capture the subject, a light source device 32 that emits illumination light to the inside of the subject through the endoscope 31, a processor device 33, and a monitor 34 for displaying a medical image such as an endoscopic image or the like captured by using the endoscope 31. The light in a specific wavelength band that is used as illumination light by the endoscope 31 is, for example, light in a shorter wavelength band than the green wavelength band. In particular, the light in a specific wavelength band is light in a blue band or a violet band of the visible range.

The processor device 33 comprises a medical image acquisition unit 35, a medical image analysis processing unit 36, and a display control unit 37. The medical image acquisition unit 35 acquires a medical image output from the endoscope 31. The medical image analysis processing unit 36 performs analysis processing on the medical image acquired by the medical image acquisition unit 35. The processing content of the medical image analysis processing unit 36 is the same as the processing content of the medical image analysis processing unit 12 of the image processing system 10. The display control unit 37 displays the medical image obtained by the medical image analysis processing unit 36 on the monitor 34 (display unit). The processor device 33 is connected to the image processing system 10. The medical image acquisition unit 35 is the same as the medical image acquisition unit 11, the medical image analysis processing unit 36 is the same as the medical image analysis processing unit 12, and the display control unit 37 is the same as the display control unit 15.

Figure 3:
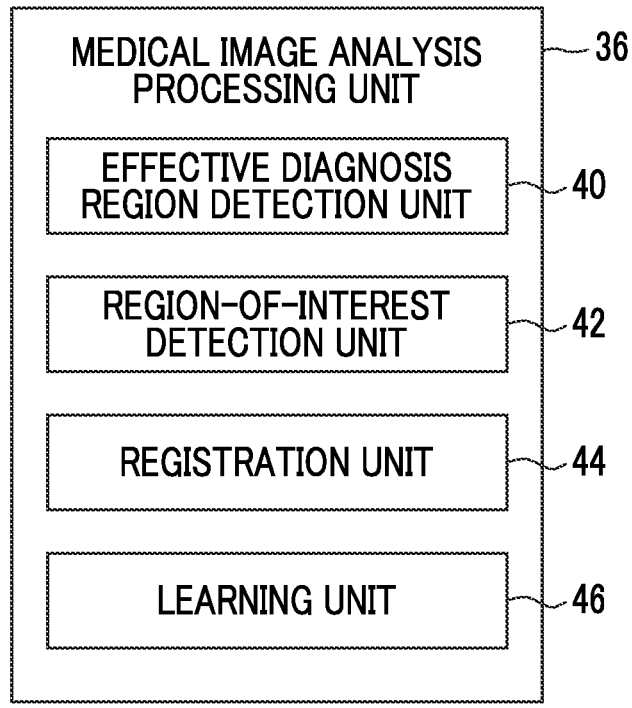
FIG. 3 is a block diagram showing a function of a medical image analysis processing unit.

The medical image analysis processing unit 36 performs analysis processing using the medical image acquired by the medical image acquisition unit 11. As shown in FIG. 3, the medical image analysis processing unit 36 comprises an effective diagnosis region detection unit 40, a region-of-interest detection unit 42, a registration unit 44, and a learning unit 46.

Figure 4:
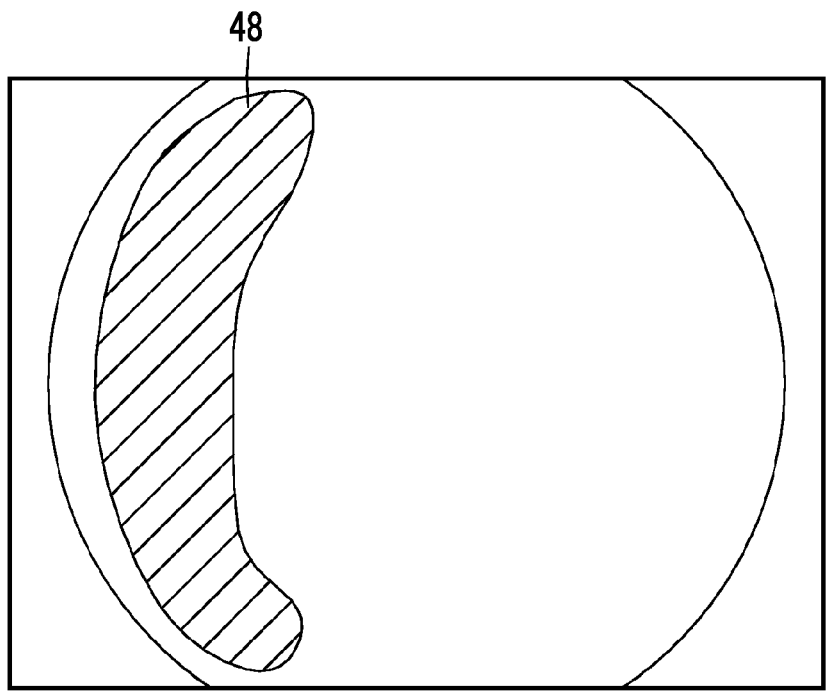
FIG. 4 is an image diagram of a first medical image having a specific pool.

The effective diagnosis region detection unit 40 detects an effective diagnosis region in which a non-target region of interest other than a region of interest is removed from an observation target, which is a region that may include a region of interest to be diagnosed by a user, from a first medical image used for detecting the effective diagnosis region among the medical images. Here, the region of interest is a region of interest to the user, and indicates a region of interest for diagnosis if the user is a doctor. Specifically, the region of interest is a lesion area or the like. The non-target region of interest is an object that is clearly different from the object included in the region of interest to be diagnosed by a user. The non-target region of interest includes, for example, if the region of interest is a lesion area, a specific pool 48 such as a puddle or a blood pool covering the observation target is included, as shown in FIG. 4. The effective diagnosis region detection unit 40 detects a region in which the specific pool 48 is removed as an effective diagnosis region for the first medical image shown in FIG. 4.

Figure 5:
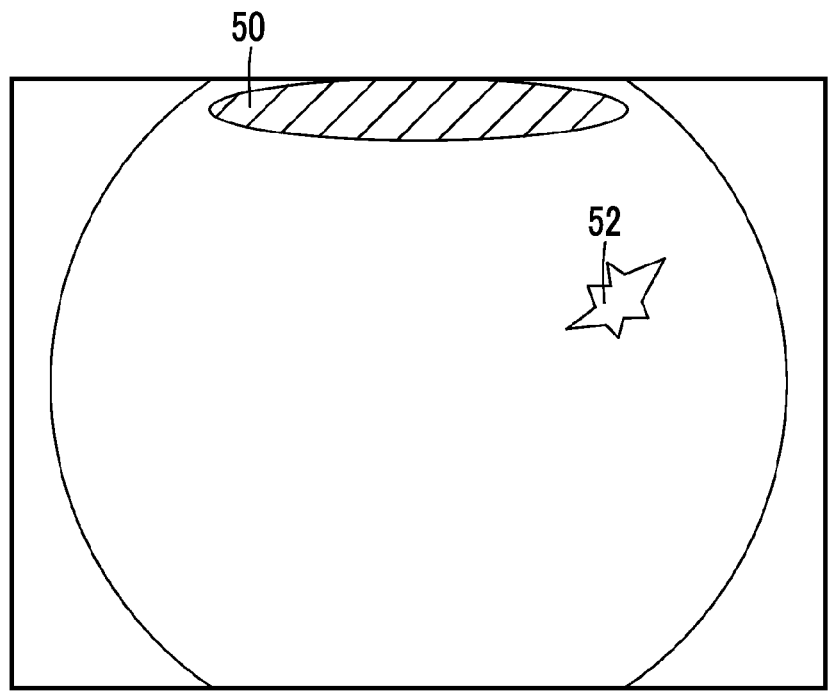
FIG. 5 is an image diagram of the first medical image having an image peripheral portion and a specular reflection portion.
Figure 6:
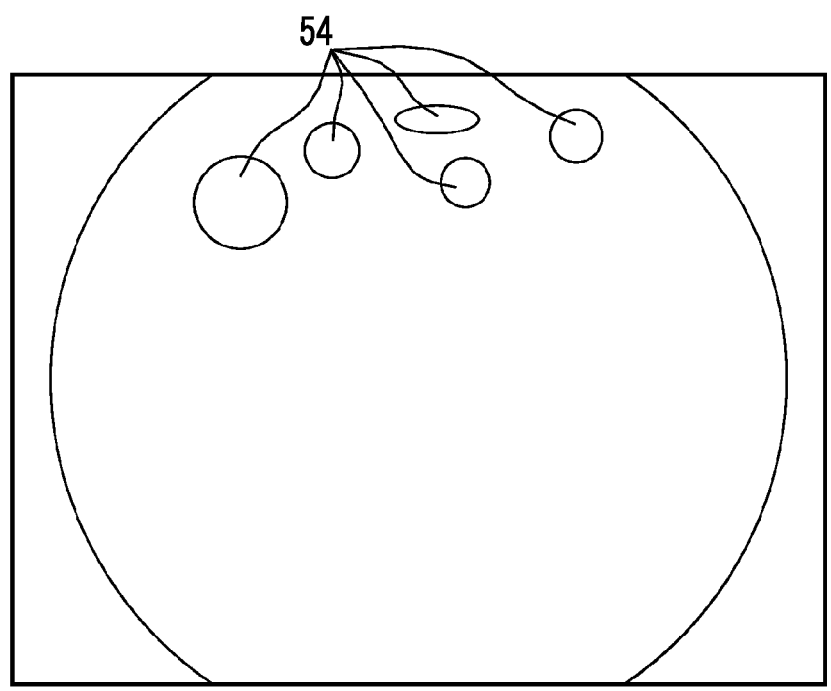
FIG. 6 is an image diagram of the first medical image having bubbles.

Further, as shown in FIG. 5, the non-target region of interest includes distortion (distortion due to an objective lens used for imaging the observation target) and image blur generated in an image peripheral portion 50. Further, the non-target region of interest includes a specular reflection 52 caused by the observation target being covered with a transparent mucous membrane. The effective diagnosis region detection unit 40 detects a region in which distortion and image blur of the image peripheral portion 50 have been removed as an effective diagnosis region for the first medical image shown in FIG. 5. In addition, as shown in FIG. 6, bubbles 54 are included in the non-target region of interest. The effective diagnosis region detection unit 40 detects a region in which the bubbles 54 have been removed as an effective diagnosis region for the first medical image shown in FIG. 6.

Figure 7:
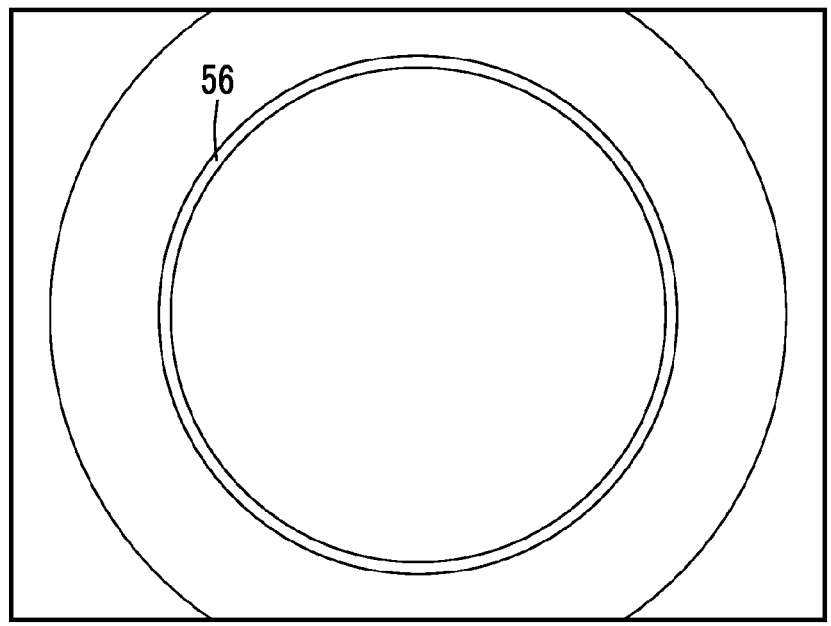
FIG. 7 is an image diagram of the first medical image in which an edge of a cap is reflected.

Further, in a case where a cap is attached to the distal end of the insertion part of the endoscope 31 and an edge 56 of the cap is reflected on the medical image as shown in FIG. 7, the non-target region of interest also includes an image of the edge 56 of the cap. The effective diagnosis region detection unit 40 detects a region in which the edge 56 of the cap is removed as an effective diagnosis region for the first medical image shown in FIG. 7. Since it is easy to detect the non-target region of interest as described above in a case of being illuminated with white light, the first medical image used for detecting the effective diagnosis region is preferably an image obtained by imaging an observation target illuminated with white light. Further, the first medical image may be an image obtained by imaging an observation target illuminated with blue narrow-band light, as in a second medical image described later.

Figure 8:
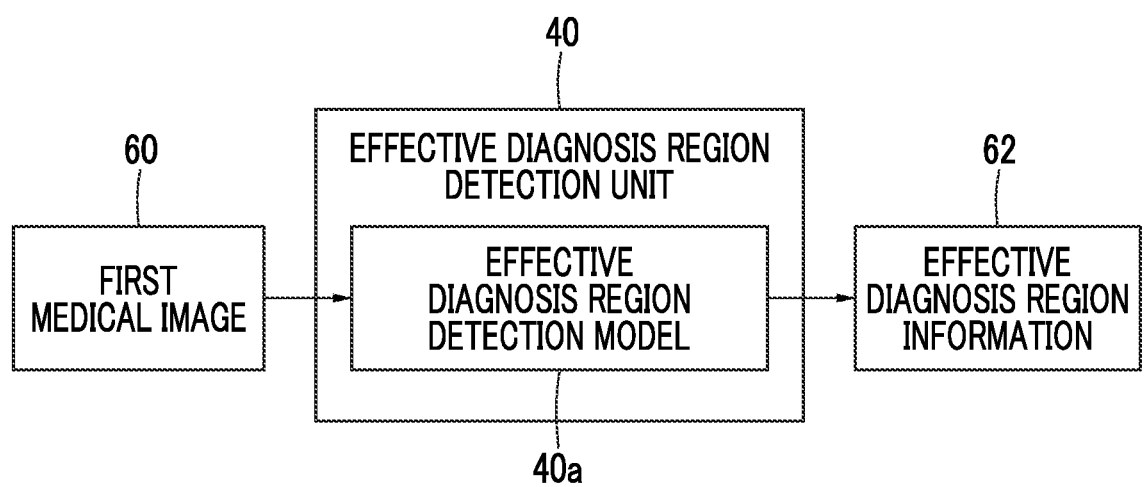
FIG. 8 is an explanatory diagram showing an effective diagnosis region detection model, the first medical image input to the effective diagnosis region detection model, and effective diagnosis region information output from the effective diagnosis region detection model.
Figure 9:
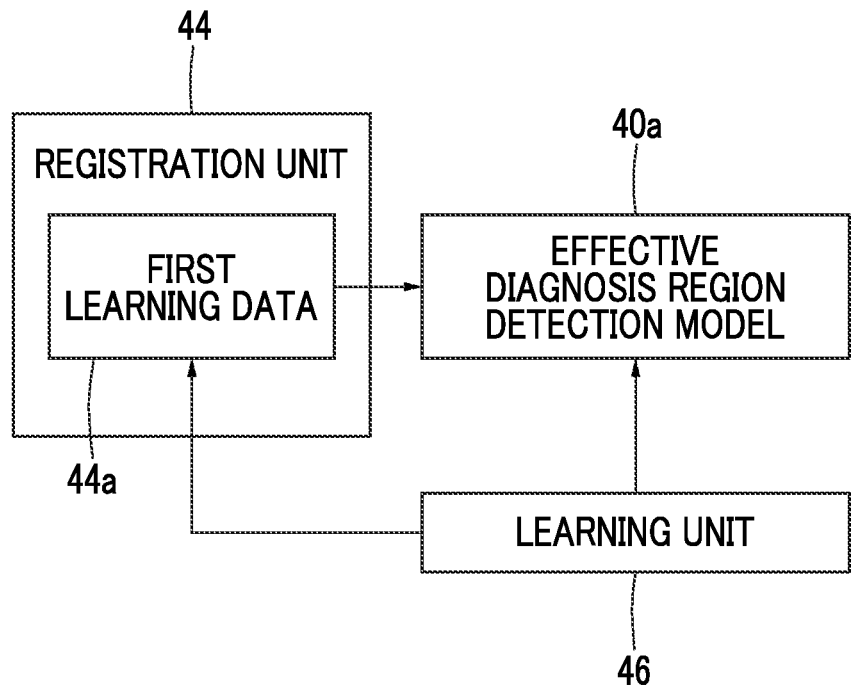
FIG. 9 is an explanatory diagram used for describing learning for the effective diagnosis region detection model.

As shown in FIG. 8, the effective diagnosis region detection unit 40 comprises an effective diagnosis region detection model 40a obtained by learning using first learning data including the first medical image and effective diagnosis region information regarding the effective diagnosis region. The effective diagnosis region detection model 40a outputs effective diagnosis region information 62 regarding the effective diagnosis region, specifically, position information occupied by the effective diagnosis region in a first medical image 60 in response to an input of the first medical image. The output effective diagnosis region information 62 enables detection of the effective diagnosis region. As shown in FIG. 9, the effective diagnosis region detection model 40a is generated in the learning unit 46 by using a machine learning method such as deep learning. Specifically, the learning unit 46 uses first learning data 44a registered in the registration unit 44 as teaching data to train the effective diagnosis region detection model 40a.

Figure 10:
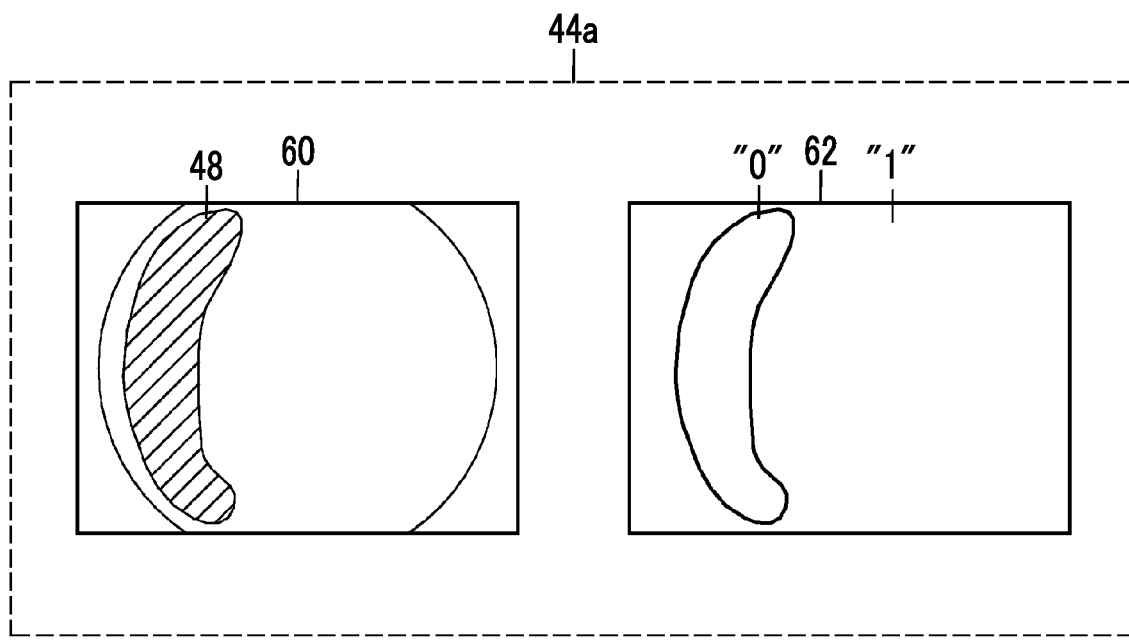
FIG. 10 is an explanatory diagram showing first learning data.

For example, in the case of the first medical image 60 having the specific pool 48 as shown in FIG. 10, it is preferable that binarized data in which a region of the specific pool 48 in the first medical image is set to a flag "0" indicating that it is not an effective diagnosis region, and a region other than the specific pool 48 is set to a flag "1" indicating that it is an effective diagnosis region is used as the effective diagnosis region information 62. Here, it is preferable that the flags "0" and "1" are designated by the user operating a user interface (not shown) connected to the endoscope system 21. In addition, for regions that can be detected by image processing of the processor device 33, such as dark areas and the specular reflection 52 (see FIG. 5) of non-target regions of interest, it is possible to automatically generate the first medical image by automatically designating the flags "0" and "1". The first medical image 60 and the effective diagnosis region information 62 described above are registered in the registration unit 44 as the first learning data 44a in which they are associated with each other. The first learning data 44a registered in the registration unit 44 is used for the effective diagnosis region detection model 40a.

As described above, not only the specific pool 48, but also the non-target regions of interest such as the image blur (see FIG. 5), the specular reflection 52 (see FIG. 5), the bubbles 54 (see FIG. 6), the edge 56 of the cap (see FIG. 7), the residue, and the residual liquid can be discriminated not only by a doctor who diagnoses a lesion or the like, but also by researchers who develop the endoscope system 21. Therefore, since the effective diagnosis region can be designated by more related parties such as researchers, the first learning data 44a can be created more than second learning data 44b described later.

The region-of-interest detection unit 42 detects a region of interest from an effective diagnosis region RX of a second medical image used for detecting the region of interest among the medical images, based on the detection result of the effective diagnosis region detection unit 40. Specifically, the region-of-interest detection unit 42 detects a region of interest only in the effective diagnosis region RX (flag "1") of the second medical image, and does not detect the region of interest in a region RY (flag "0") other than the effective diagnosis region. Here, the region of interest detected by the region-of-interest detection unit 42 is a region including a lesion area represented by a cancer, a benign tumor area, an inflammation area (including a portion with changes such as bleeding or atrophy in addition to a so-called inflammation), colon diverticulum, treatment scars (endoscopic mucosal resection (EMR) scars, endoscopic submucosal dissection (ESD) scars, clip points), bleeding points, perforations, vascular dysplasia, a cauterization scar due to heating or a marking area marked by coloring with a coloring agent, a fluorescent agent, or the like, or a biopsy area where biopsy examination (so-called biopsy) is performed. That is, a region including a lesion, a region having a possibility of a lesion, a region where any treatment such as a biopsy is performed, a treatment tool such as clips or forceps, a region which is required to be observed in detail regardless of a possibility of a lesion, such as a dark region (back of folds, a region where observation light is difficult to reach due to the depth of the lumen), or the like can be a region of interest. In the endoscope system 21, the region-of-interest detection unit 42 detects a region including at least one of a lesion area, a benign tumor area, an inflammation area, a diverticulum of a large colon, a treatment scar, a bleeding point, a perforation, a vascular dysplasia marking area, or a biopsy area, as the region of interest.

In detecting a lesion region among the regions of interest, in a case where illumination is performed with blue narrow-band light, for example, narrow-band light having a wavelength band of 400 nm to 450 nm, it becomes easy to detect structural information useful for specifying a lesion region, such as a vascular structure or a ductal structure. Accordingly, the second medical image used for detecting a region of interest is preferably an image obtained by imaging an observation target illuminated with blue narrow-band light. Here, in a case where the first medical image is a white light image and the second medical image is a blue narrow-band light image, the timing of imaging is different between the first medical image and the second medical image because the white light and the blue narrow-band light are alternately illuminated for imaging. Therefore, it is preferable to align the first medical image and the second medical image, and then set the effective diagnosis region for the first medical image and the second medical image. For example, in a case where the effective diagnosis region of the first medical image is detected first, it is preferable to set a region of the second medical image corresponding to the effective diagnosis region of the first medical image as the effective diagnosis region. In the image alignment, it is preferable to perform an alignment process on the first medical image so as to match the shape of the second medical image. As with the first medical image, the second medical image may be an image obtained by imaging an observation target illuminated with white light.

Figure 11:
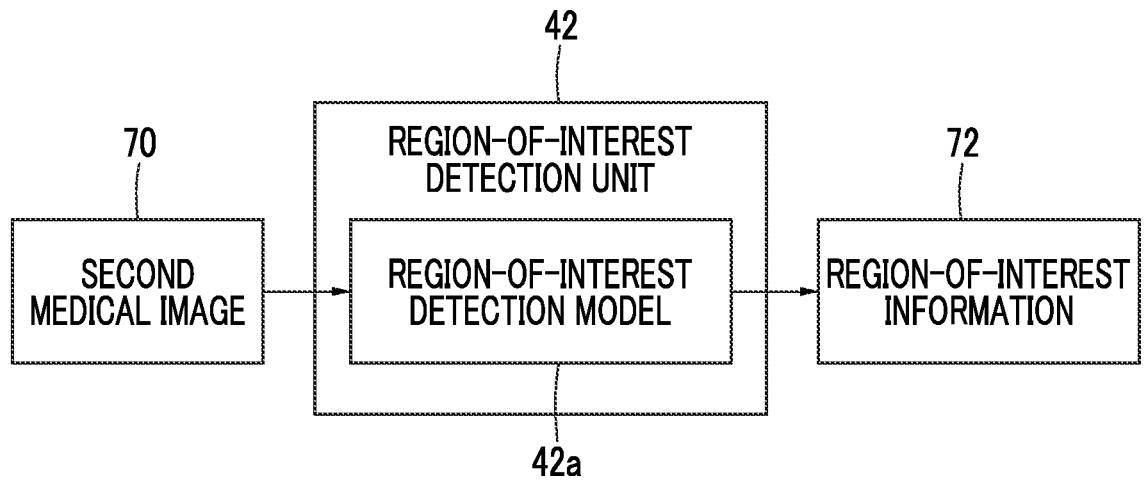
FIG. 11 is an explanatory diagram showing a region-of-interest detection model, a second medical image input to the region-of-interest detection model, and region-of-interest information output from the region-of-interest detection model.
Figure 12:
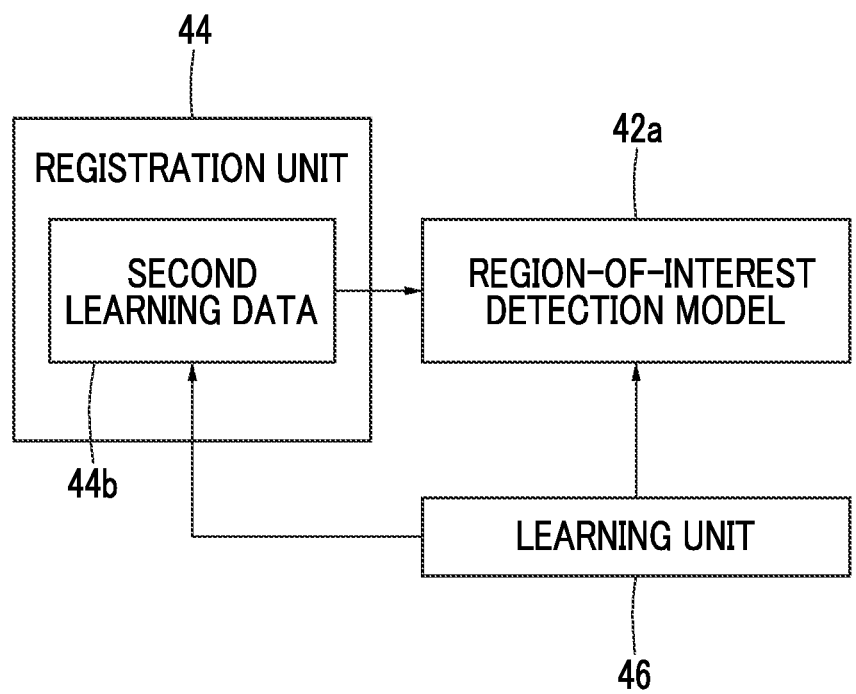
FIG. 12 is an explanatory diagram used for describing learning for the region-of-interest detection model.

As shown in FIG. 11, the region-of-interest detection unit 42 comprises a region-of-interest detection model 42a obtained by learning using second learning data including the second medical image and region-of-interest information regarding the region of interest. The region-of-interest detection model 42a outputs region-of-interest information 72 regarding the region of interest, specifically, position information occupied by the region of interest in a second medical image 70 in response to an input of the second medical image. The output region-of-interest information 72 enables detection of the region of interest. As shown in FIG. 12, the region-of-interest detection model 42a is generated in the learning unit 46 by using a machine learning method such as deep learning. Specifically, the learning unit 46 uses the first learning data 44a registered in the registration unit 44 as teaching data to train the region-of-interest detection model 42a.

Figure 13:
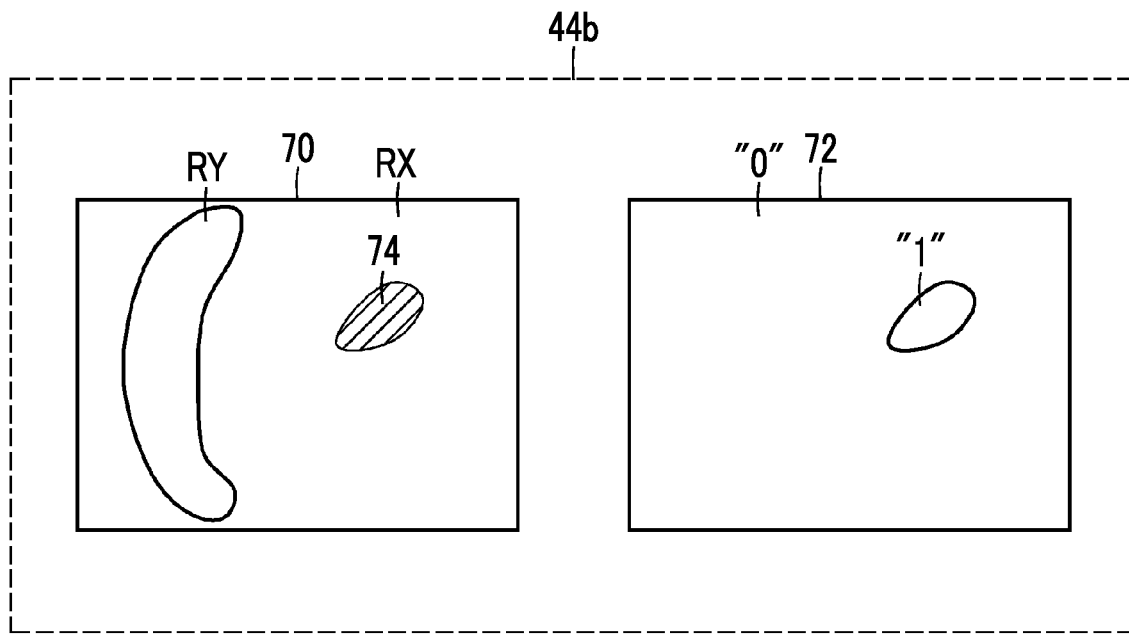
FIG. 13 is an explanatory diagram showing second learning data.

For example, in the case of the second medical image 70 having a specific lesion area 74 as shown in FIG. 13, it is preferable that binarized data in which a region other than the specific lesion area 74 in the second medical image 70 is set to a flag "0" indicating that it is not a region of interest, and a region of the specific lesion area 74 is set to a flag "1" indicating that it is a region of interest is used as the region-of-interest information 72. Here, it is preferable that the flags "0" and "1" are designated by operating a user interface (not shown) connected to the endoscope system 21 according to the instructions of a user who has knowledge in diagnosing the region of interest, such as a doctor. The second medical image 70 and the region-of-interest information 72 described above are registered in the registration unit 44 as the second learning data 44b in which they are associated with each other. The second learning data 44b registered in the registration unit 44 is used for learning the region-of-interest detection model 42a.

As described above, since the region-of-interest detection unit 42 detects the region of interest from the effective diagnosis region in which the non-target region of interest is removed, compared with the case where the region of interest is detected from the image in which the non-target region of interest is not removed, the detection accuracy of the region of interest is improved by removing the feature that causes learning noise. That is, in the present embodiment, by performing "detection of the non-target region of interest (detection other than the effective diagnosis region)" and "detection of the region of interest" separately, it is possible to reduce the number of learning data items required for detecting the region of interest such as a lesion, so that the detection accuracy of the region of interest can be finally improved.

Figure 14:
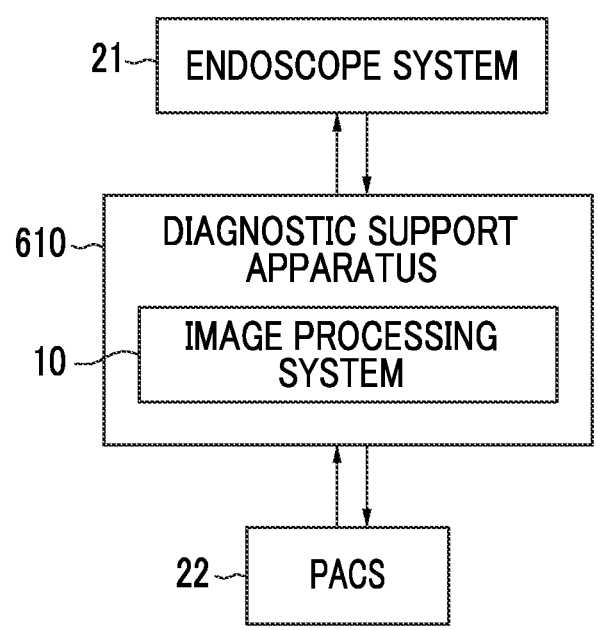
FIG. 14 is a diagnostic support apparatus including the image processing system.
Figure 15:
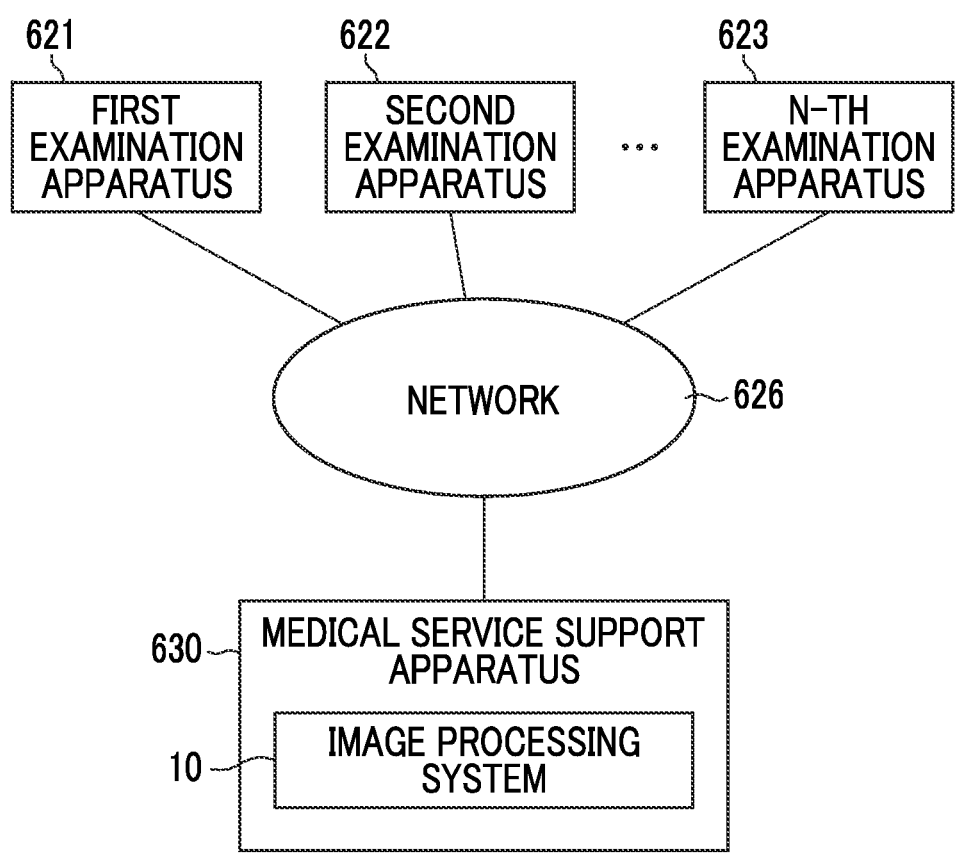
FIG. 15 is a medical service support apparatus including the image processing system.

In addition, as shown in FIG. 14, a diagnostic support apparatus 610 used in combination with the endoscope system 21, other modalities, and the PACS 22 can include the image processing system 10 of the above embodiment and other modification examples. In addition, as shown in FIG. 15, for example, a medical service support apparatus 630 connected to various examination apparatuses including the endoscope system 21, such as a first examination apparatus 621, a second examination apparatus 622, . . . , and an N-th examination apparatus 623, through a certain network 626 can include the image processing system 10 of the above embodiment and other modification examples.

In the above embodiment, the effective diagnosis region detection unit 40 distinguishes and detects the effective diagnosis region and the non-target region of interest other than the effective diagnosis region, but may distinguish and detect a plurality of types of non-target regions of interest. For example, bubbles, specular reflections, images of the periphery of the cap, or normal squamous epithelium are separately distinguished and detected as non-target regions of interest. In this case, the region in which the detected bubbles, specular reflection, the images of the periphery of the cap, or the normal squamous epithelium are removed is set as the effective diagnosis region, and the region of interest is detected from this effective diagnosis region.

In addition, the image processing system 10, the endoscope system 21, and various devices or systems including the image processing system 10 can be used with the following various modifications.

As the medical image, it is possible to use a normal light image obtained by emitting light in a white band or light in a plurality of wavelength bands as light in the white band.

In a case where an image obtained by emitting light in a specific wavelength band is used as the medical image, a band narrower than the white wavelength band can be used as the specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition unit that acquires a special light image having a signal in a specific wavelength band on the basis of a normal light image obtained by emitting light in a white band or light in a plurality of wavelength bands as light in the white band. In this case, the special light image can be used as the medical image.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as light in the white band or the special light image obtained by emitting light in a specific wavelength band. In this case, the feature amount image can be used as the medical image.

In the endoscope system 21, a capsule endoscope can be used as the endoscope 31. In this case, the light source device 32 and a part of the processor device 33 can be mounted in the capsule endoscope.

In the above embodiment and modification examples, hardware structures of processing units for executing various kinds of processing, such as the medical image acquisition unit 11, the medical image analysis processing unit 12, each unit forming the medical image analysis processing unit 12, the display control unit 15, the input receiving unit 16, the overall control unit 17, the medical image acquisition unit 35, the medical image analysis processing unit 36, the display control unit 37, the effective diagnosis region detection unit 40, the region-of-interest detection unit 42, the registration unit 44, and the learning unit 46, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a circuit configuration designed exclusively for executing various types of processing, a graphical processing unit (GPU), and the like.

One processing unit may be configured by one of various processors, or may be configured by a combination of two or more processors of the same type or different types (for example, a combination of a plurality of FPGAs, a combination of a CPU and an FPGA, or a combination of a CPU and a GPU). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as hardware structures.

More specifically, the hardware structure of these various processors is an electrical circuit (circuitry) in the form of a combination of circuit elements, such as semiconductor elements. The hardware structure of the storage unit is a storage device such as a hard disc drive (HDD) or a solid state drive (SSD).

The present invention can be implemented by the following alternative embodiment.

A processor device including:
a medical image acquisition unit that acquires a first medical image obtained by imaging an observation target;
an effective diagnosis region detection unit that detects an effective diagnosis region in which a non-target region of interest other than a region of interest is removed from the observation target, from the first medical image; and
a region-of-interest detection unit that detects the region of interest from the effective diagnosis region,
in which, in a case where the effective diagnosis region detection unit detects the effective diagnosis region, the effective diagnosis region detection unit detects the effective diagnosis region from the first medical image, by using an effective diagnosis region detection model obtained by learning using first learning data including the first medical image and effective diagnosis region information regarding the effective diagnosis region.

EXPLANATION OF REFERENCES

10: image processing system
11: medical image acquisition unit
12: medical image analysis processing unit
13: display unit
15: display control unit
16: input receiving unit
17: overall control unit
18: saving unit
21: endoscope system
22: PACS
31: endoscope
32: light source device
33: processor device
34: monitor
35: medical image acquisition unit
36: medical image analysis processing unit
37: display control unit
40: effective diagnosis region detection unit
40a: effective diagnosis region detection model
42: region-of-interest detection unit
42a: region-of-interest detection model
44: registration unit
44a: first learning data
44b: second learning data
46: learning unit
48: specific pool
50: image peripheral portion
52: specular reflection
54: bubble
56: edge
60: first medical image
62: effective diagnosis region information
70: second medical image
72: region-of-interest information
74: lesion area
610: diagnostic support apparatus
621: first examination apparatus
622: second examination apparatus
623: N-th examination apparatus
626: network
630: medical service support apparatus

What is claimed is:

1. A medical image processing system comprising:
a processor configured to function as:
a medical image acquisition unit that acquires a first medical image obtained by imaging an observation target;
an effective diagnosis region detection unit that detects an effective diagnosis region in which a non-target region of interest other than a region of interest is removed from the observation target, from the first medical image; and
a region-of-interest detection unit that detects the region of interest from the effective diagnosis region,
wherein the effective diagnosis region detection unit detects the effective diagnosis region from the first medical image, by using an effective diagnosis region detection model obtained by learning using first learning data including the first medical image and effective diagnosis region information regarding the effective diagnosis region,
the medical image acquisition unit acquires a second medical image obtained with illumination light having a wavelength band different from that for obtaining the first medical image, and
the region-of-interest detection unit detects the region of interest from the effective diagnosis region of the second medical image.

2. The medical image processing system according to claim 1,
wherein the region-of-interest detection unit detects the region of interest from the effective diagnosis region, by using a region-of-interest detection model obtained by learning using second learning data including the effective diagnosis region and the region of interest.

3. The medical image processing system according to claim 1,
wherein the first medical image is obtained by imaging an observation target illuminated with white light.

4. The medical image processing system according to claim 1,
wherein the second medical image is obtained by imaging an observation target illuminated with blue narrow-band light.

5. The medical image processing system according to claim 1, wherein the non-target region of interest includes a puddle, a blood pool, a dark area, a specular reflection, distortion, image blur, a bubble, a cap, a residue, and a residual liquid.

6. A medical image processing system comprising:

a processor configured to function as:

a registration unit that registers first learning data including a first medical image obtained by imaging an observation target and effective diagnosis region information regarding an effective diagnosis region in which a non-target region of interest other than a region of interest is removed from the observation target; and a learning unit that performs learning for generating an effective diagnosis region detection model that outputs the effective diagnosis region in response to an input of the first medical image, by using a plurality of pieces of the first learning data.

7. The medical image processing system according to claim 6, wherein the registration unit registers second learning data including the effective diagnosis region and the region of interest, and the learning unit performs learning for generating a region-of-interest detection model that outputs the region of interest in response to an input of the effective diagnosis region, by using the second learning data.

8. A learning method comprising:

a first learning step of performing, by a processor, learning for generating an effective diagnosis region detection model that outputs an effective diagnosis region in response to an input of a first medical image, by using a plurality of pieces of first learning data including the first medical image obtained by imaging an observation target and effective diagnosis region information regarding the effective diagnosis region in which a non-target region of interest other than a region of interest is removed from the observation target.

9. The learning method according to claim 8, further comprising:

a second learning step of performing, by the processor, learning for generating a region-of-interest detection model that outputs the region of interest in response to an input of the effective diagnosis region, by using a plurality of pieces of second learning data including the effective diagnosis region and the region of interest.

* * * * *